US011298165B2

(12) United States Patent
Nardini (10) Patent No.: US 11,298,165 B2
(45) Date of Patent: *Apr. 12, 2022

(54) SELF CENTERING FEATURE FOR AN INTRAMEDULLARY NAIL

(71) Applicant: DePuy Synthes Products, Inc., Raynham, MA (US)

(72) Inventor: Reto Nardini, Oberdorf (CH)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 516 days.

This patent is subject to a terminal disclaimer.

(21) Appl. No.: 16/026,933

(22) Filed: Jul. 3, 2018

(65) Prior Publication Data

US 2018/0310971 A1 Nov. 1, 2018

Related U.S. Application Data

(62) Division of application No. 13/647,834, filed on Oct. 9, 2012, now Pat. No. 10,039,582.

(60) Provisional application No. 61/577,991, filed on Dec. 20, 2011.

(51) Int. Cl.
*A61B 17/80* (2006.01)
*A61B 17/72* (2006.01)
*A61B 17/86* (2006.01)
*A61B 17/68* (2006.01)
*A61B 17/17* (2006.01)

(52) U.S. Cl.
CPC ........ *A61B 17/7241* (2013.01); *A61B 17/725* (2013.01); *A61B 17/7233* (2013.01); *A61B 17/8052* (2013.01); *A61B 17/8057* (2013.01); *A61B 17/863* (2013.01); *A61B 17/1725* (2013.01); *A61B 17/68* (2013.01)

(58) Field of Classification Search
CPC ... A61B 17/8061; A61B 17/725; A61B 17/72; A61B 17/7283; A61B 17/7241; A61B 17/7258

See application file for complete search history.

(56) References Cited

U.S. PATENT DOCUMENTS

| 5,861,041 A * | 1/1999 | Tienboon | A61F 2/4455 623/17.16 |
|---|---|---|---|
| 2011/0022049 A1 * | 1/2011 | Huebner | A61B 17/8052 606/71 |
| 2013/0090656 A1 * | 4/2013 | Huebner | A61B 17/1735 606/281 |

(Continued)

*Primary Examiner* — Ellen C Hammond
(74) *Attorney, Agent, or Firm* — Fay Kaplun & Marcin, LLP (57) ABSTRACT

An intramedullary nail includes a body sized and shaped for insertion into a medullary canal of a bone and extending along a longitudinal axis from a proximal end to a distal end and a channel extending through the body along the longitudinal axis in combination with a locking hole extending laterally through the body along a central axis and in communication with the channel, the locking hole defined by a first opening extending through a first portion of a wall of the nail and a second opening extending through a second portion of the wall substantially opposing the first portion, the first opening being elongated in a lateral direction relative to the longitudinal axis of the nail and the second opening including a coupling element configured to lock a portion of a bone fixation element therein.

15 Claims, 8 Drawing Sheets

(56) References Cited

U.S. PATENT DOCUMENTS

2014/0052258 A1\* 2/2014 Ball ................. A61F 2/442
                                                    623/17.16
2016/0324652 A1\* 11/2016 Brow ............. A61B 17/8052

\* cited by examiner

SELF CENTERING FEATURE FOR AN INTRAMEDULLARY NAIL

PRIORITY CLAIM

The present application is a Divisional Application of U.S. patent application Ser. No. 13/647,834, now U.S. Pat. No. 10,039,582 filed on Oct. 9, 2012, which claims priority to U.S. Provisional Application Ser. No. 61/577,991 filed on Dec. 20, 2011. The disclosure of the above patent(s)/application(s) is incorporated herein by reference.

BACKGROUND

Intramedullary nails are inserted into the medullary canals of long bones to stabilize these bones (e.g., to fix fractures thereof) and may include locking holes extending laterally through distal and proximal portions thereof to fix a nail at a desired position within the bone. An aiming arm may be attached to a proximal end of an intramedullary nail to aid in locating positions of the proximal and distal locking holes to guide the drilling of holes through the bone to permit the insertion of locking screws into the locking holes. Due to the natural curvature of the medullary canal, however, an intramedullary nail may bend as it is inserted moving distal locking holes out of alignment with the aiming holes in the aiming arm.

SUMMARY OF THE INVENTION

The present invention is directed to an intramedullary nail, comprising a body sized and shaped for insertion into a medullary canal of a bone and extending along a longitudinal axis from a proximal end to a distal end and a channel extending through the body along the longitudinal axis in combination with a locking hole extending laterally through the body along a central axis and in communication with the channel, the locking hole defined by a first opening extending through a first portion of a wall of the nail and a second opening extending through a second portion of the wall substantially opposing the first portion, the first opening being elongated in a lateral direction relative to the longitudinal axis of the nail and the second opening including a coupling element configured to lock a portion of a bone fixation element therein.

DETAILED DESCRIPTION

The present invention may be further understood with reference to the following description and the appended drawings, wherein like elements are referred to with the same reference numerals. The present invention relates to the stabilization of bones and, in particular, to the stabilization of a long bone (e.g., a fractured bone) using an intramedullary nail. Exemplary embodiments of the present invention describe an intramedullary nail including a distal locking hole configured such that a bone fixation element may be inserted therethrough even when the nail is bent as a result of insertion in a medullary canal of a bone. In particular, a first one of the distal locking hole extends along a central axis from a first opening in a near wall of the intramedullary nail to a second opening in a far wall. The first opening is laterally elongated so that a bone fixation element may be inserted through the locking hole at an angle with respect to the central axis. It should be noted that the terms "proximal" and "distal" as used herein, are intended to refer to a direction toward (proximal) and away from (distal) a user of the device.

An intramedullary nail 100 according to an exemplary embodiment of the present invention shown in FIGS. 1-5 comprises a locking hole 102 extending through a distal portion 104 thereof. The intramedullary nail 100 is sized and shaped for insertion in to a medullary canal of a bone 10 and extends along a longitudinal axis L from a proximal end (not shown) to a distal end 106 with a channel 108 extending therethrough along the longitudinal axis L. The locking hole 102 extends laterally through the distal portion 104 along a central axis C which, in an exemplary embodiment, is substantially perpendicular to the longitudinal axis L. The locking hole 102 extends from a first opening 110 in a first portion of a wall 112 (e.g., along a near wall) of the nail 100 to a second opening 114 in a second portion of the wall 112 (e.g., along a far wall) substantially diametrically opposed to the first portion of the wall 112. The first and second openings 110, 114 are sized and shaped to permit a bone fixation element 116 to be inserted therethrough, from the first opening 110 to the second opening 114, at an angle with respect to the central axis C such that the bone fixation element 116 may be inserted therethrough even when the bone fixation element 116 is inserted misaligned with the central axis C due, for example, to bending of the nail 100 as it conforms to the shape of the bone into which it has been inserted. In particular, the first opening 110 is elongated in a direction transverse to the longitudinal axis L of the nail 100 to permit the bone fixation element 116 to be inserted therethrough even when it is angled with respect to the central axis C. The second opening 114 is configured to engage a portion of the bone fixation element 116 therein. When the intramedullary nail 100 is bent laterally with respect to the longitudinal axis of the nail 100, as it conforms to the path of the medullary canal, the user may rely on the aiming hole in the aiming handle to drill a hole and insert the bone fixation element 116 so long as the axis of the aiming hole passes through the elongated portion of the first opening 110. That is, as the deformation of the nail 100 moves the first opening 110 substantially laterally the position of the first opening 110 along the longitudinal axis of the nail 100 is known and the elongated shape of the first opening 110 compensates for the lateral misalignment.

It will be understood by those of skill in the art that a conventional aiming arm or any other known aiming device/method may be utilized to determine a position of the locking hole 102 along a length of the nail 100. For example, a conventional aiming arm end of the nail 100 includes at least one aiming hole extending therethrough (and, preferably, one aiming hole for each bone fixation element to be inserted laterally through the nail 100). The aiming hole is positioned to be precisely aligned with the locking hole 102 prior to distortion of the nail 100 during insertion into a bone 10. As the bending of the distal portion 104 of the nail 100 is substantially lateral with respect to the longitudinal axis of the nail 100, the aiming hole still substantially indicates a position of the locking hole 102 along a length of the nail 100 even after the nail 100 has been inserted into the bone 10. A hole corresponding in position and direction to the aiming hole drilled into a near cortex of the bone 10 permits the bone fixation element 116 to be inserted into the locking hole 102 via the corresponding hole in the bone 10. The corresponding hole in the bone 10 may be overdrilled (e.g., drilled such that a diameter thereof is slightly larger than a desired diameter of the bone fixation element) to increase the chance of the bone fixation element 116 finding the elongated first opening 110.

The first opening 110 is elongated in a direction substantially perpendicular to the longitudinal axis L such that the bone fixation element 116 may be inserted therethrough even when the distal portion 104 of the nail 100 is bent. The first opening 110 according to this embodiment of the invention also includes a sharp edge 136 to facilitate cutting through any bone-ingrowth if, in the future, the intramedullary nail 100 must be removed from the bone 10. The first opening 110 may also include an angled interior surface 134 angled to guide a bone fixation element 116 inserted into the first opening 110 toward the second opening 114. The fist opening 110 is sized to provide a desired range of possible movement of the bone fixation element therein. For example, a first opening 110 having a width (e.g., a distance between lateral ends) of approximately 7.8 mm will permit a bone fixation element 116 to be inserted therethrough within a range of about 7 mm.

Figure 3:
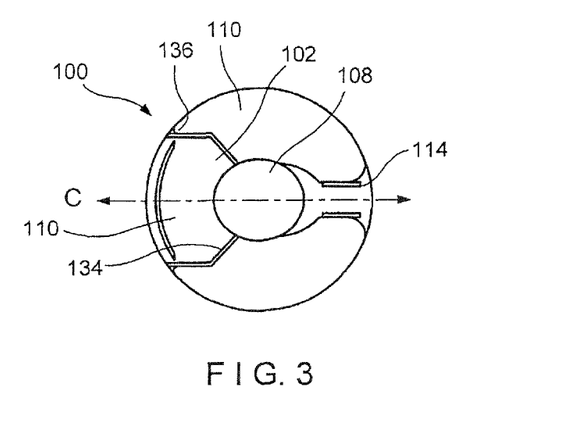
FIG. 3 shows a lateral cross-sectional view of the intramedullary nail of FIG. 1, along line A-A.
Figure 4:
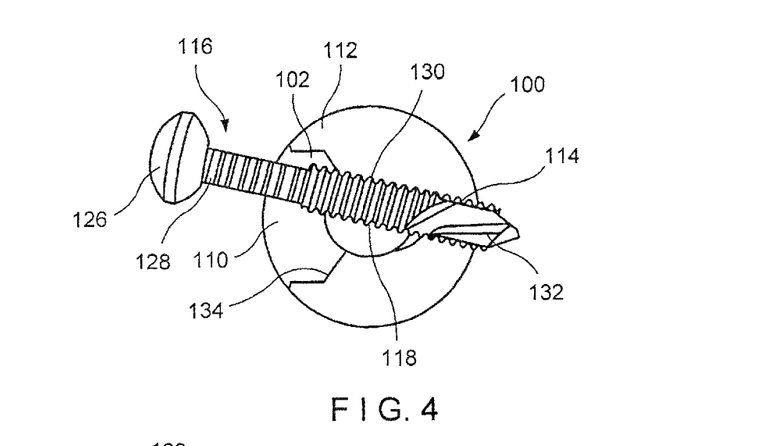
FIG. 4 shows a lateral cross-sectional view of the intramedullary nail of FIG. 1, along line A-A, with a bone fixation element extending through a locking hole thereof.
Figure 5:
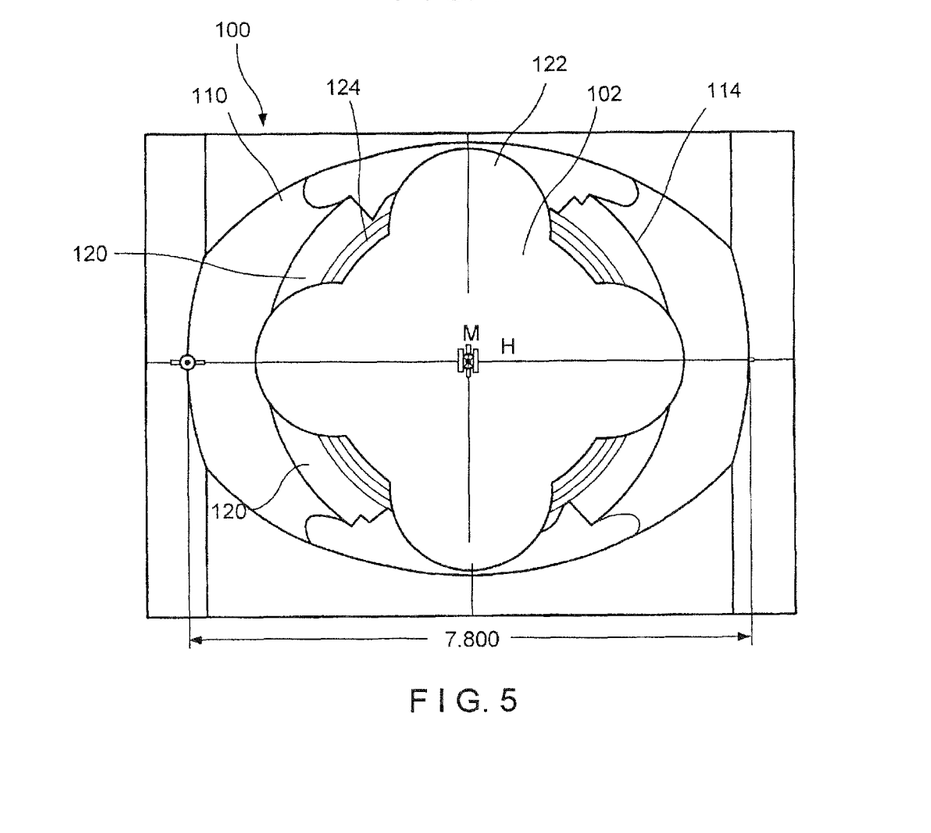
FIG. 5 shows an enlarged side view of the distal portion of the intramedullary device of FIG. 1.

The second opening 114 is sized, shaped and configured to receive and lock a portion of the bone fixation element 116. The second opening 114 according to this embodiment includes a coupling element permitting a portion of the bone fixation element 116 to be locked therein even when the bone fixation element 116 extends therethrough at an angle with respect to the central axis C. The second opening 114 may, for example, be configured as a variable angle hole which engages threads 118 of the bone fixation element 116 even when the bone fixation element 116 is angled with respect to the central axis C. For example, the second opening 114 may include a plurality of columns 120 separated from one another about a circumference of the opening 114 and extending radially inward therefrom. Each of the columns 120 is separated from adjacent columns via scalloped portions 122 which extend radially outward therefrom. In one exemplary embodiment, the columns 120 are spaced substantially equidistantly from one another about a circumference of the second opening 114. The columns 120 include protrusions 124 such as, for example, threads or spikes, extending therefrom to engage the threading 118 of the bone fixation element 116. Each of the columns 120 according to this embodiment includes a surface curving and/or tapering radially inward permitting the protrusions 124 to engage the threads 118 while the bone fixation element 116 is inserted along an axis at any angle (within a permitted range of angulation) relative to the central axis C of the locking hole 102. For example, the bone fixation element 116 may be inserted through the locking hole 102 at an angle up to 15° relative to the central axis C.

Figure 6:
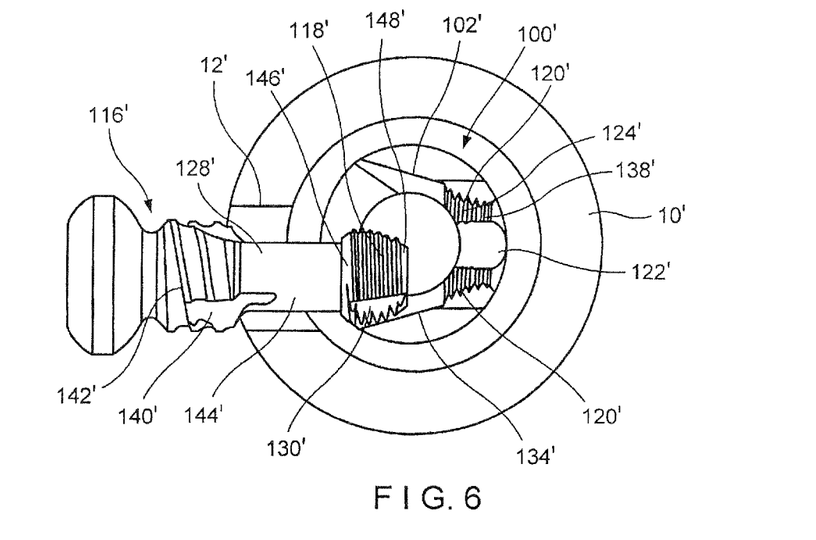
FIG. 6 shows a lateral cross-sectional view of an intramedullary nail and a bone fixation element being inserted into a locking hole thereof according to a further embodiment of the present invention.
Figure 7:
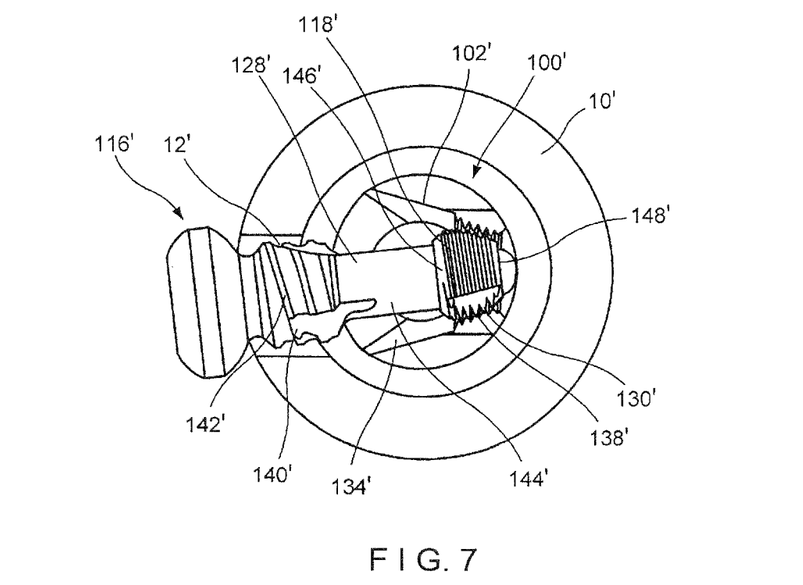
FIG. 7 shows a lateral cross-sectional view of the intramedullary nail of FIG. 6, with the bone fixation element engaging the locking hole.

In one particular embodiment, as shown in FIGS. 6-7, protrusions 124' are formed in columns 120' along a second opening 114' of a locking hole 102'. The protrusions 124' are formed as parts of a thread 138' which, if connected across scalloped portions 122' of the second opening 114', would form a single helical thread 138' extending thereabout. Thus, as described above, a bone fixation element 116' may be inserted through the locking hole 102' at an angle relative to a central axis C' thereof. In particular, an enlarged distal portion 130' of the bone fixation element 116' may contact an angled surface 134' of the first opening 110' such that the distal portion 130' of the bone fixation element 116' is guided toward the second opening such that threading 118' therealong engages the thread 138' of the second opening 114'.

Although the exemplary embodiment specifically describes a variable angle hole, it will be understood by those of skill in the art that the second opening 114 and/or bone fixation element 116 may include coupling elements other than the variable angle hole described above so long as the coupling element permits the bone fixation element 116 to extend therethrough at an angle with respect to the central axis C. For example, in another embodiment, the bone fixation 116 may be cannulated such that a wire may be received therein. The wire may include an enlarged distal end such that when the wire is pulled proximally relative to the bone fixation element 116, the enlarged distal end is received within the cannulation, causing a portion of the bone fixation element 116 to expand radially outward and engage an inner surface of the locking hole 102.

Figure 1:
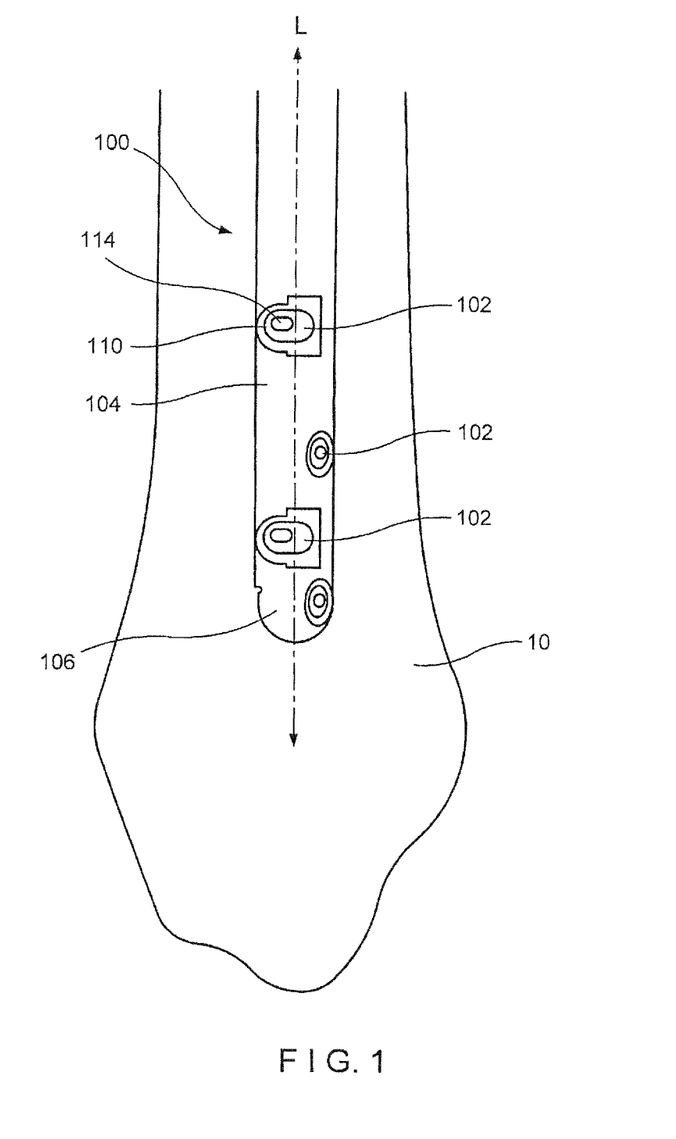
FIG. 1 shows a side view of a distal portion of an intramedullary nail according to an exemplary embodiment of the present invention.
Figure 2:
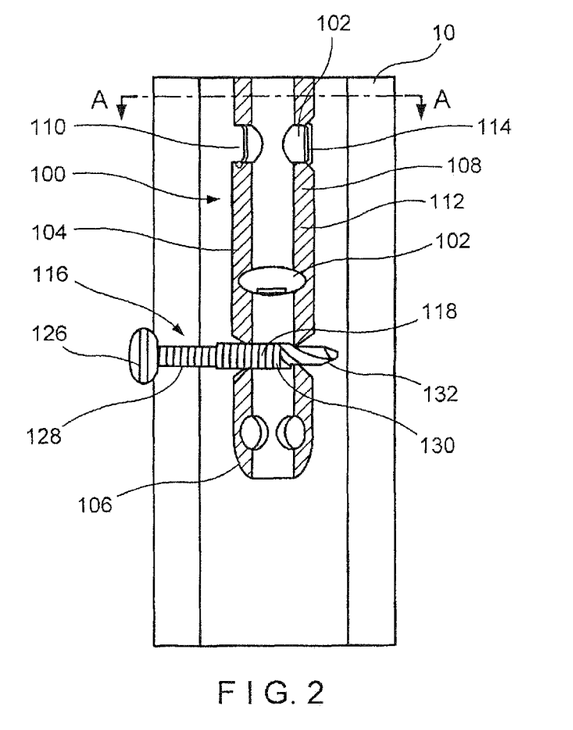
FIG. 2 shows a longitudinal cross-sectional view of the distal portion of the intramedullary nail of FIG. 1.

In one embodiment, as shown in FIGS. 2 and 4, the bone fixation element 116 includes a head portion 126 and a shaft 128 extending distally therefrom. The shaft 128 includes an enlarged distal portion 130 with a self-drilling tip 132 at a distal end thereof and threading 118 extending therealong. The self-drilling tip 132 may include blades extending therealong for cutting a bone as it is inserted into the bone. A length of the bone fixation element 116 is selected so that the threading 118 along the enlarged distal portion 130 engages the coupling element (e.g., protrusions 124 of a variable angle hole) of the second opening 114. Thus, the bone fixation element 116 provides monocortical fixation of the intramedullary nail 100 such that it may be desired to utilize at least three bone fixation elements 116 to fix the intramedullary nail 100 to the bone 10.

Thus, the intramedullary nail 100 may include a plurality of locking holes 102 extending through the distal portion 104 spaced apart from one another along a length of the nail 100 and angled with respect to one another about the longitudinal axis L. In a preferred embodiment, the intramedullary nail 100 may include at least three locking holes 102 extending through the distal portion 104. Each of the locking holes 102 is configured to receive a bone fixation element 116, as described above.

In cases in which a hole is drilled in the bone, the self-drilling tip 132 is not required. In another embodiment, as shown in FIGS. 6 and 7, a bone fixation element 116' may be substantially similar to the bone fixation element 116 except that it does not include the self-drilling tip 132 and further includes an enlarged proximal portion 140' along a shaft 128' thereof in addition to an enlarged distal portion 130'. The enlarged distal portion 130' tapers from a proximal end 146' to a distal end 148' thereof and may have a curved exterior surface such that threads 118' extending therealong engage the protrusions 124' as the bone fixation element 116' is inserted through the locking hole 102' at an angle relative to the central axis C'. The enlarged proximal portion 140' is sized to engage a hole 12' drilled in a bone 10' and includes threading 142' therealong for engaging the drilled hole. The enlarged proximal portion 140' is separated from the enlarged distal portion 130' along the shaft 128' via an unthreaded middle portion 144' having a smaller diameter than both the proximal and distal portions 140', 130'. Although the bone fixation element 116' is specifically shown and described as being inserted into the locking hole 102, it will be understood by those of skill in the art that either of the bone fixation elements 116, 116' may be utilized for either of the holes 102, 102'.

Figure 8:
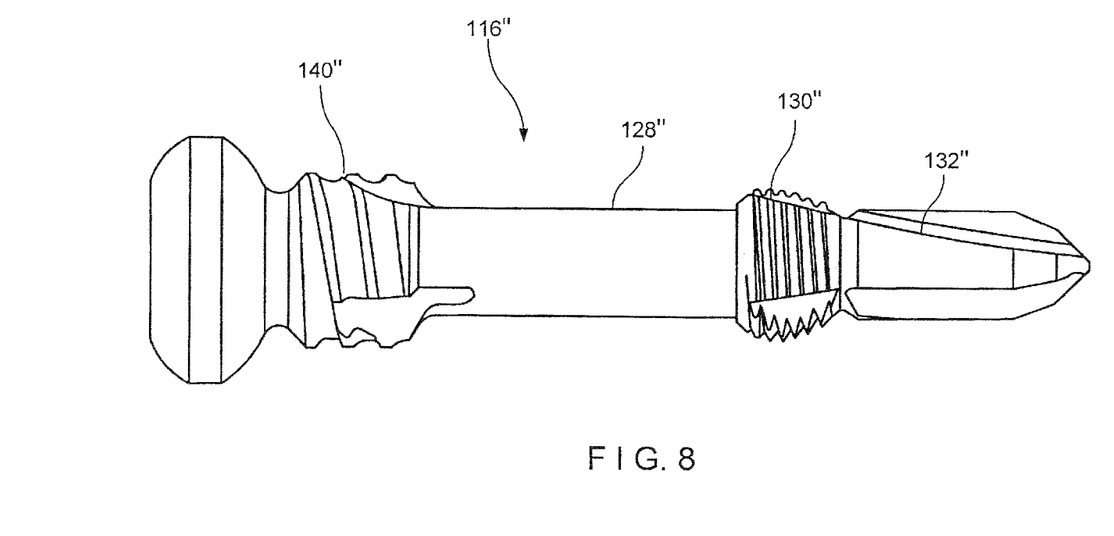
FIG. 8 shows a side view of a bone fixation element according to another embodiment of the present invention.

In another embodiment, as shown in FIG. 8, a bone fixation element 116" is substantially similar to the bone fixation elements 116' described above, comprising a shaft 128" including a threaded proximal portion 140" separated from a threaded distal portion 130" by an unthreaded middle portion 144". The bone fixation element 116", however, also comprises a self-drilling tip 132" substantially similar to the self-drilling tip 132 of the bone fixation element 116. The self-drilling tip 132" may include blades extending therealong for cutting a bone as it is inserted into the bone. It will be understood by those of skill in the art that the bone fixation element 116" may be utilized in either of the locking holes 102, 102' described above.

According to an exemplary surgical technique of the present invention, an intramedullary nail 100 is inserted into the medullary canal of the bone 10. A conventional aiming arm or other aiming device is coupled to the nail 100 to facilitate the locating of the locking hole 102 (i.e., an axis of an aiming hole extends along the central axis C). Using the aiming hole as a guide, a hole is drilled into the near cortex of the bone 10 and the bone fixation element 116 is inserted into the corresponding hole in the bone 10 and into the enlarged first opening 110. As the bone fixation element 116 is inserted through the locking hole 102, a distal end thereof contacts the angled interior surface 134 such that the bone fixation element 116 is guided through the second opening 114 at an angle relative to the central axis C, within the permitted range of angulation. The threading 118 along the enlarged portion 130 engages the protrusions 124, or other coupling element, of the second opening 114, fixing the bone fixation element within the locking hole 102. The above-described process may be repeated for each of the remaining locking holes 102 extending through the nail 100. As discussed above, either of the bone fixation elements 116', 116" may be inserted into the locking hole 102 in place of the bone fixation element 116.

Figure 9:
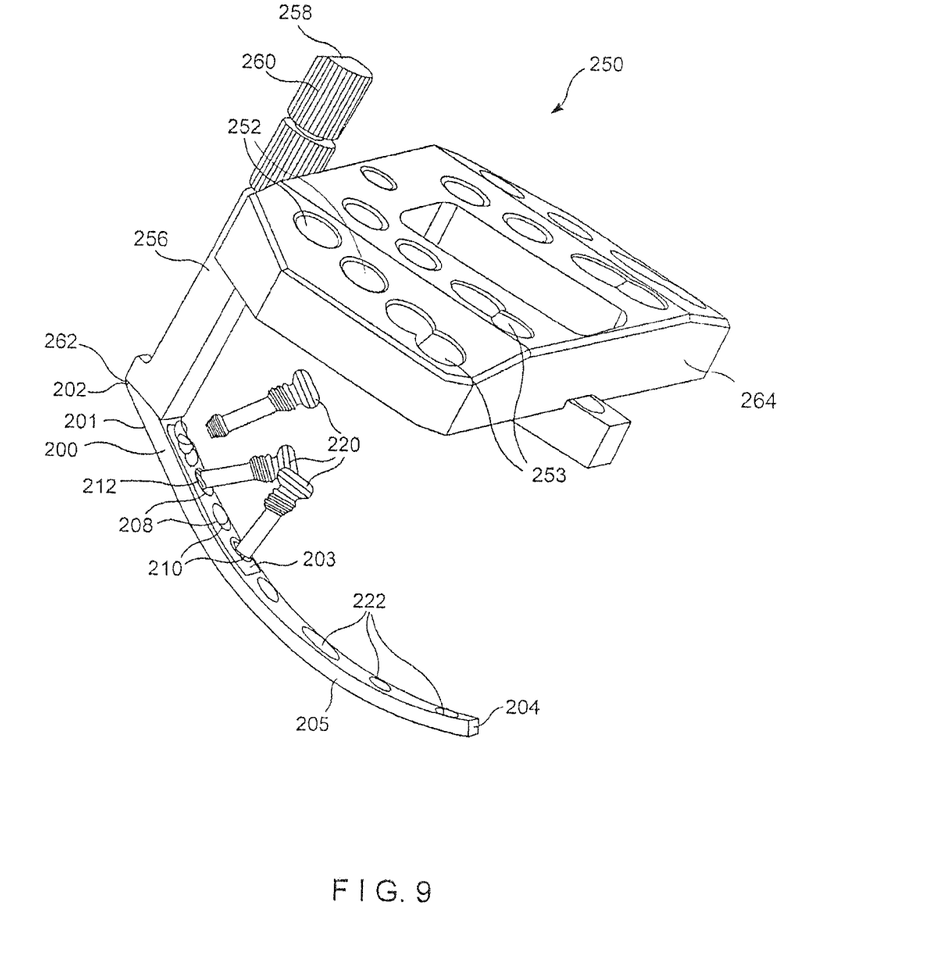
FIG. 9 shows a side view of an intramedullary plate according to another embodiment of the invention.
Figure 10:
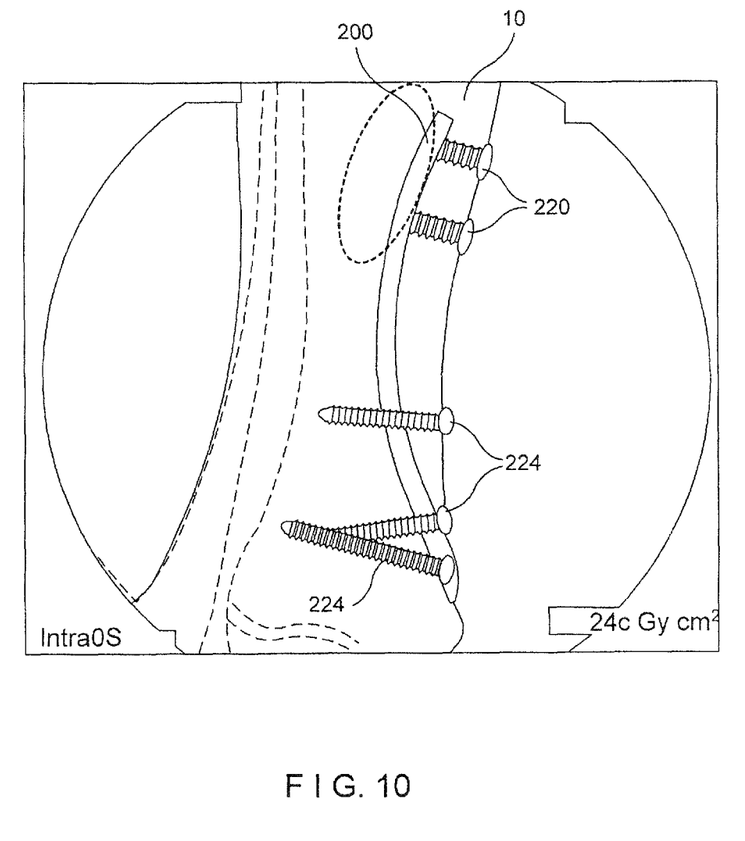
FIG. 10 shows a cross-sectional view of the intramedullary plate of FIG. 9 after implantation into a bone.

FIGS. 9-10 depict an intramedullary bone plate 200 according to another embodiment of the invention. The intramedullary bone plate 200 is formed substantially similarly to the intramedullary nail 100 except as noted below. The intramedullary plate 200 is sized and shaped for insertion into a medullary canal of a bone 10 and extends along an arcuate path from a proximal end 202 to a distal end 204. However, unlike the intramedullary nail 100, a cross-sectional shape of the intramedullary plate 200 is substantially rectangular, with substantially smooth edges to minimize trauma to the bone, as those skilled in the art will understand. It is noted, however, that other cross-sectional shapes are envisioned within the scope of the invention. The proximal end 202 is configured to removably engage an aiming arm 250 to aid in insertion of bone fixation elements 220 into the intramedullary plate 200, as will be described in greater detail later on. Specifically, the proximal end 202 may include an opening (not shown) configured to permit insertion of a threaded locking mechanism extending through a handle 256 of the aiming arm 250. Specifically, the handle 256 extends from a first end 258 having a knob 260 connected to an elongated shaft (not shown) to a second end 262 having an opening (not shown) configured for alignment with the proximal opening (not shown) of the plate 200. In an operative configuration, the second end 262 is aligned with the proximal opening (not shown) of the plate 200 and rotated to cause the shaft (not shown) to extend out of the second end 262 and into the proximal opening. At least a portion of the shaft (not shown) may be threaded to engage corresponding threads of the proximal opening (not shown). It is noted, however, that other engagement means are envisioned within the scope of the invention, including, but not limited to, a friction-fit engagement.

A proximal portion 201 of the intramedullary plate 200 is fitted with an insert 203 having a plurality of locking holes 208 extending therethrough. Specifically, the insert 203 is positioned over a recess (not shown) formed on a side wall of the plate 200, the recess having a thickness smaller than a thickness of the plate 200. The insert 203 is dimensioned so that, when positioned over the recess, an outer wall of the insert 203 lies flush with an outer wall of the plate 200, as shown in FIG. 9. Thus, the locking holes 208 extending through the insert 203 terminate at the plate 200 so that the bone fixation element 220 inserted therethrough does not extend through the plate 200 and out of an opposing wall thereof. Rather, the locking holes 208 are closed at their distal ends by a wall of the plate 200. Each of the locking holes 208 extends from a first opening 210 in a first portion of a wall 212 (e.g., along a near wall) to a second opening (not shown) terminating within the bone plate 200. As those skilled in the art will understand, this configuration prevents a bone fixation element 220 inserted through the locking hole 208 from extending through the intramedullary plate 200 and entering the far cortex. The locking hole 208 includes threading configured to threadedly engage threading 118, 118', 130" of the bone fixation element 220, as described in greater detail in earlier embodiments. The insert 203 may be integrally formed with the plate 200 or may be attached thereto using any known attachment means.

In an alternate embodiment, each of the locking holes 208 may extend along a locking hole axis C substantially perpendicular to a longitudinal axis of the intramedullary plate 200 at the point at which the hole 208 passes through the plate 200 (i.e., a line tangent to the arc of the plate 200 at the hole 208). Each of the first openings 210 and the second openings (not shown) is sized and shaped to permit a bone fixation element 220 to be inserted therethrough at an angle with respect to the central axis C such that the bone fixation element 220 may be inserted therethrough even if the bone fixation element 220 is misaligned with the central axis C.

The bone fixation element 220 is formed substantially similarly to the bone fixation element 116' described earlier. A length of the bone fixation element 220 is selected to precisely correspond to a distance from the near cortex to the second opening (not shown) after implantation. The first opening 210 is elongated in a direction transverse to the longitudinal axis L of the plate 200 to permit the bone fixation element 220 to be inserted therethrough even when angled with respect to the central axis C. The second opening (not shown) is configured to engage a portion of the bone fixation element 220 therein. The second opening (not shown) is substantially similar to the second opening 114 and is sized, shaped and configured to receive and lock a portion of the bone fixation element 220. Specifically, the second opening 114 includes a coupling element permitting a portion of the bone fixation element 220 to be locked therein even when the bone fixation element 220 extends therethrough at an angle with respect to the central axis C. The second opening (not shown) may, for example, be configured as a variable angle hole which engages threads 118 of the bone fixation element 220 or may include a plurality of columns separated of ridges from one another about a circumference of the second opening by scalloped portions which extend radially outward therefrom, as described in greater detail in earlier embodiments. In this embodiment, a guide plate 264 of the aiming arm 250 may also comprise a variable angle hole 253 to aid in alignment with the indicated locking hole 208.

The intramedullary plate 200 may also comprise a plurality of additional locking holes 222 in a distal portion 205 thereof. The locking holes 222 are arranged at various angles relative to one another and have geometries selected to permit engagement thereof with bone fixation screws 224. The locking holes 222 may be substantially similar to any of the locking holes 102, 208 disclosed herein.

According to an exemplary surgical technique of the present invention, the intramedullary plate 200 is inserted into the medullary canal of the bone 10. The aiming arm 250 is coupled to the plate 200 to facilitate locating the locking holes 208. Using the aiming holes 252, 253 as a guide, a hole is drilled into the near cortex of the bone 10 and the bone fixation element 220 is inserted into the corresponding hole in the bone 10 and into the enlarged first opening 210. A bone fixation element 220 having a length corresponding to a distance from the near cortex of the bone to the second opening (not shown) of a selected locking hole 208 is inserted through the locking hole 208, a distal end thereof contacting an angled interior surface of the locking hole 208 (not shown) such that the bone fixation element 220 is guided to the second opening (not shown) at an angle relative to the central axis C, within the permitted range of angulation. The above-described process may be repeated for each of the remaining locking holes 208 extending through the plate 200. The plate 200 according to the invention is configured so that, when bent laterally with respect to the longitudinal axis L as it conforms to the path of the medullary canal, the user may rely on the aiming hole 252, 253 in the aiming arm 250 to drill a hole and insert the bone fixation element 220 so long as the axis of the aiming hole 252, 253 passes through the elongated portion of the first opening 210. The exemplary plate 200 according to the invention is particularly suited for insertion into the distal tibia which has a substantially oval cross-section. The substantially rectangular cross-sectional shape of the plate 200 is therefore well-suited for insertion into the distal tibia. The bone fixation element 220 is inserted into the locking hole 208 until a distal end thereof contacts the proximal portion 201 of the bone plate 200, wherein the distal end may be substantially blunt and/or angled to maximize a contacting surface are thereof with the proximal portion 201. Insertion of the bone fixation elements 220 against the intramedullary plate 200 also provides a stable interface therewith. Furthermore, by locking the bone fixation element 220 relative to the intramedullary plate 200, there is no possibility of the bone fixation element 220 damaging soft tissue, organs, etc. at an opposing wall of the bone, as may be experienced with certain bicortical systems.

Figure 11:
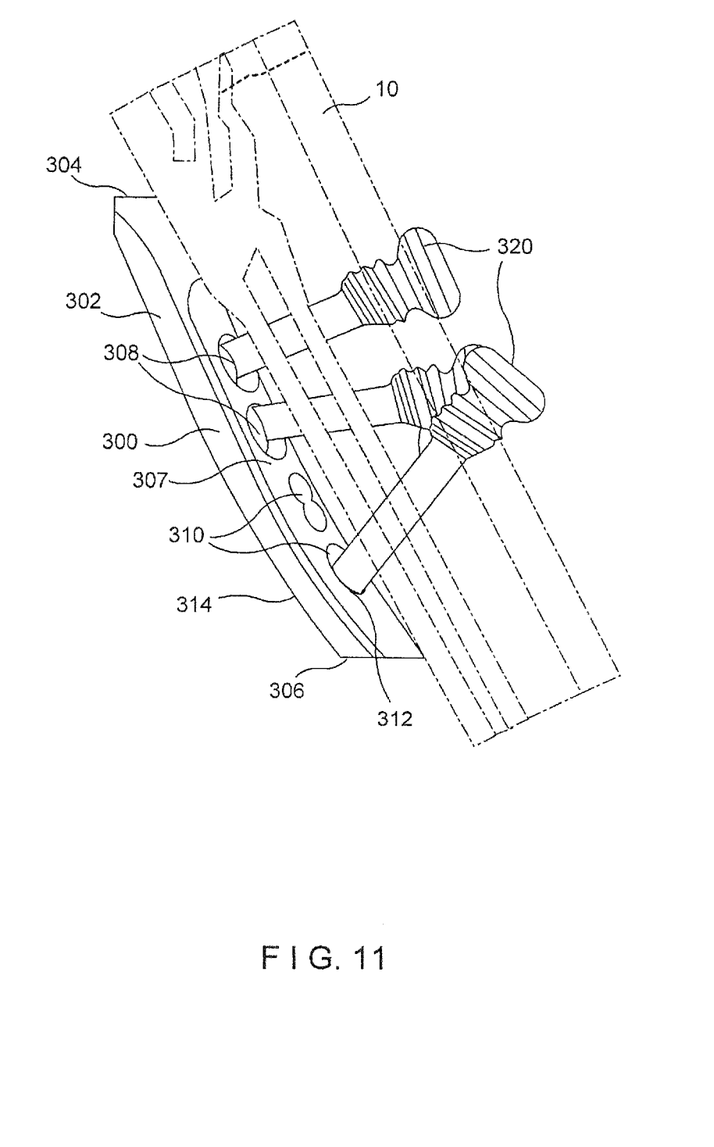
FIG. 11 shows a partial see-through view of a bone plate according to yet another embodiment of the invention.

FIG. 11 depicts a device according to another embodiment of the invention and includes a bone plate 300 configured for placement over the far cortex in combination with bone fixation elements 320 inserted through the near cortex. The bone plate 300 includes an elongate body 302 extending from a first end 304 to a second end 306, dimensions thereof being selected to conform to the requirements of a particular procedure. An insert 307 is positioned over a proximal portion of the bone plate 300 and includes a plurality of locking holes 308 extending therethrough from a first opening 310 on a first wall 312 positioned over the far cortex in an operative configuration to a second opening (not shown) on a second wall (not shown) positioned over the proximal portion of the bone plate 300. Similar to the bone plate 200, the insert 307 prevents the bone fixation element 320 inserted through the locking hole 308 from exiting out of the plate 300 and into the body. That is, a second wall 314 of the bone plate 300 is substantially smooth with no openings. The locking holes 308 are substantially similar to the locking holes 102, 208 described earlier and are dimensioned to lockingly engage threads of the bone fixation element 320 even when the bone fixation element 320 is angled with respect to a central axis C thereof. Thus, the bone fixation elements 320 inserted through the insert 307 are prevented from being inserted through the proximal portion of the bone plate 300. The bone fixation element 320 is also formed substantially similar to the bone fixation elements 116, 220 described above.

In accordance with an exemplary surgical technique according to the invention, the first wall 312 is positioned over the far cortex of a target portion of the bone via a minimally invasive incision and provisionally secured thereto using a method known in the art. An imaging technique known in the art may then be used to aid in insertion of bone fixation elements 320 into the near cortex and through the bone to align with a selected one of the locking holes 308. When treating smaller bones (e.g., bones of the hand, etc.), a surgeon or other user may have direct access to the near cortex and may manually guide the insertion of the bone fixation elements 320 into the bone. As described in greater detail earlier, a length of each of the bone fixation elements 320 is determined prior to insertion conforming to a total distance from the near cortex to the second opening (not shown) of the locking hole 308. The bone fixation element 320 is then inserted into the bone until a head thereof is seated over the bone and threads (not shown) provided at a distal end thereof lockingly engage threads of the locking hole 308. As those skilled in the art will understand, not having the bone plate 300 placed on the near cortex prevents disturbance thereof after implantation given the thin layer of soft tissue covering the near cortex. This thin layer of tissue over the near cortex prevents the placement of a conventional bone plate and screw thereover. The exemplary system and method of the invention provides increased freedom in plate and screw placement and further biomechanically optimizes plate placement to a region having the least lever arm.

It will be apparent to those skilled in the art that various modifications and variations can be made in the structure and the methodology of the present invention without departing from the spirit or scope of the invention. Thus, it is intended that the present invention cover the modifications and variations of this invention provided that they come within the scope of the appended claims and their equivalents.

What is claimed:

1. A system for bone fixation, comprising:
a plate body sized and shaped for placement at a first target location of a bone, the plate body extending along a longitudinal axis from a proximal end to a distal end;
an insert received within a recess of the plate body, the insert including a first insert locking hole extending laterally through the insert along a central axis, a first plate body locking hole being aligned with the first insert locking hole and extending a distance into the plate body to terminate at a closed end within the plate body;
a first bone fixation element including a head, a shaft and a threaded portion, the first bone fixation element being insertable through the bone to extend through the first insert locking hole into the first plate body locking hole so that the threaded portion engages a locking feature of the first plate body locking hole; and wherein the first target location is a medullary canal and the plate body is an intramedullary plate.

2. The system of claim 1, wherein the first insert locking hole is elongated in a lateral direction relative to the longitudinal axis of the plate body.

3. The system of claim 2, wherein the first insert locking hole includes an interior surface angled to guide the first bone fixation element toward the first plate body locking hole.

4. The system of claim 2, wherein the first insert locking hole is substantially perpendicular to the longitudinal axis.

5. The system of claim 2, wherein the first plate body locking hole is a variable angle hole including a plurality of columns separated from one another and extending radially inward, the columns including protrusions extending therealong to engage the threaded portion of the bone fixation element that is inserted through the first insert_locking hole at an angle within a permitted range of angulations relative to the central axis.

6. The system of claim 2, wherein the shaft of the bone fixation element includes an enlarged distal portion with a threading extending thereabout to engage the first insert locking hole at an angle within a permitted range of angulations relative to the central axis.

7. The system of claim 6, wherein the shaft includes an enlarged proximal portion separated from the enlarged distal portion by an unthreaded middle portion having a smaller diameter than the enlarged proximal and distal portions, the enlarged proximal portion having a threading extending thereabout to engage a hole drilled in a bone.

8. The system of claim 6, further comprising a self-drilling tip extending distally from the enlarged distal portion.

9. The system of claim 6, wherein the enlarged distal portion tapers from a proximal end to a distal end thereof or includes a curved exterior surface.

10. The system of claim 1, wherein a length of the first bone fixation element is selected to correspond to a distance from an outer surface of the cortex of the bone and the first plate body locking hole when the plate body is in a desired location within a bone.

11. The system of claim 1, wherein the first plate body locking hole is open only in a direction facing the insert.

12. The system of claim 1, wherein the central axis of the first plate body locking hole is substantially perpendicular to the longitudinal axis of the plate at the first plate body locking hole.

13. The system of claim 1, wherein the locking feature is a threading corresponding to the threaded portion of the first bone fixation element.

14. The system of claim 1, further comprising:
an aiming arm removably engaging the proximal end of the plate body, the aiming arm including a handle extending from a first end to a second end and a guide plate comprising a plurality of aiming holes to align with the first insert locking holes.

15. The system of claim 14, wherein the handle further includes a threaded locking mechanism extending therethrough to attach the handle to the plate body.

* * * * *